(12) United States Patent
Cournand

(10) Patent No.: US 8,324,903 B2
(45) Date of Patent: Dec. 4, 2012

(54) FLUID CONDUCTIVITY SENSOR FOR ACTUATING AND TESTING AN ELECTROEXPLODING DEVICE

(75) Inventor: Andre Cournand, Safety Harbor, FL (US)

(73) Assignee: Conax Florida Corporation, St. Petersburg, FL (US)

( * ) Notice: Subject to any disclaimer, the term of this patent is extended or adjusted under 35 U.S.C. 154(b) by 357 days.

(21) Appl. No.: 12/646,137

(22) Filed: Dec. 23, 2009

(65) Prior Publication Data

US 2011/0148394 A1    Jun. 23, 2011

(51) Int. Cl.
*G01N 27/02* (2006.01)
*G01R 27/22* (2006.01)
(52) U.S. Cl. ............................ 324/439; 324/444; 324/92
(58) Field of Classification Search .............. 324/92–94, 324/439–450
See application file for complete search history.

(56) References Cited

U.S. PATENT DOCUMENTS

| | | | | |
|---|---|---|---|---|
| 4,680,537 A | * | 7/1987 | Miller | 324/500 |
| 4,703,280 A | | 10/1987 | Miller | |
| 4,827,844 A | * | 5/1989 | Miller | 102/220 |
| 4,853,637 A | * | 8/1989 | Endres | 324/439 |
| 5,289,132 A | * | 2/1994 | Oksman et al. | 324/444 |
| 6,644,098 B2 | * | 11/2003 | Cardinale et al. | 73/25.01 |
| 6,683,464 B2 | * | 1/2004 | Park et al. | 324/706 |
| 7,372,277 B2 | * | 5/2008 | Diamond et al. | 324/444 |
| 8,030,942 B2 | * | 10/2011 | Diamond et al. | 324/444 |

* cited by examiner

*Primary Examiner* — Joshua Benitez Rosario
(74) *Attorney, Agent, or Firm* — GrayRobinson, P.A.; Michael J. Colitz, III

(57) ABSTRACT

Disclosed is an apparatus for sensing the electrical conductivity of fluid wherein when electrodes of the apparatus are exposed to fluid. When the electrodes are exposed to a fluid with a predetermined salinity, a voltage is developed on a capacitor which in turn fires a load, such as a resistive bridge wire. Also disclosed is a testing circuit, whereby the integrity of the circuit can be ascertained without the necessity of actually firing the circuit.

14 Claims, 2 Drawing Sheets

FLUID CONDUCTIVITY SENSOR FOR ACTUATING AND TESTING AN ELECTROEXPLODING DEVICE

BACKGROUND OF THE INVENTION

1. Field of the Invention

This invention relates to a circuit for sensing the electrical conductivity of fluid and for firing an associated device upon sensing a fluid with a predetermined conductivity. More specifically, the present invention relates to improved means for test firing such a circuit without the need for triggering the device.

2. Description of the Background Art

The use of fluid conductivity sensors for use as actuators is known. These sensors have been used in detonating electro explosive devices for releasing various mechanisms, such as mechanisms for uncoupling a parachute canopy upon landing in water.

An example of one such device is disclosed in U.S. Pat. No. 4,853,637 to Endres, entitled "Fluid Conductivity Sensor for Actuating an Electroexploding Device." Another example is illustrated in U.S. Pat. No. 4,703,280 to Miller, entitled "Fluid Conductivity Sensor Controlling an Electro Explosive Device." Both these references are assigned to the assignee of the present invention. The contents of both applications are incorporated herein by reference.

An important consideration in the design of such release mechanisms is preventing accidental detonation arising, for example, from exposure of the sensor to rain. On the other hand, once the valid condition for detonation is satisfied, i.e. landing in a body of water, it is desirable to have the detonation occur as rapidly as possible.

In addition to providing specific measures to accomplish the foregoing, it would be highly desirable to provide for use with such release mechanisms conductivity sensing devices having the smallest possible number of components to enhance the probability of achieving the highest possible reliability.

Sensors such as those described in the Endres and Miller patents suffer from an inability to fully test the operability and integrity of the circuit. Historically, the only way to fully assure the operatability of the sensor was to actually initiate a firing sequence. This, however, was undesirable in that conductivity sensors are not designed to be reused after completion of a firing sequence. Thus, there exists a need in the art to provide a means for testing the operability and integrity of a conductivity sensor without detonating the associated explosive device.

SUMMARY OF THE INVENTION

It is, therefore, a primary object of this invention to provide a new and improved means for testing a circuit that is designed to sense the electrical conductivity of a fluid.

It is another object of this invention to provide a new and improved means for test firing an explosive detatonator circuit without the need for an explosive detatonation.

It is an additional object of this invention to provide a new and improved apparatus for sensing the electrical conductivity of fluid.

It is a further object of this invention to provide such apparatus which is highly reliable in operating in response to fluid having a predetermined condition of electrical conductivity and not being susceptible to inadvertent or accidental operation in response to fluid not having such predetermined condition of conductivity.

It is a further object of this invention to provide such apparatus which operates relatively rapidly in response to sensing fluid having such predetermined condition of electrical conductivity.

It is a further object of this invention to provide such apparatus having the fewest possible number of components so as to enhance the probability of achieving highly reliable operation.

It is a further object of this invention to provide such apparatus which is relatively simple in structure and is relatively economical to produce.

It is a further object of this invention to provide such apparatus for use with an electro explosive device of a release mechanism for uncoupling a parachute canopy from its load upon landing in water.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

The present invention relates to an apparatus for sensing the electrical conductivity of fluid. When the electrodes are exposed to a fluid with a predetermined salinity, a voltage is developed on a capacitor which, in turn, fires a load which can be a release mechanism. Also disclosed is a testing circuit, whereby the integrity of the sensing circuit can be confirmed without the need for firing the load or triggering the release mechanism.

Figure 1:
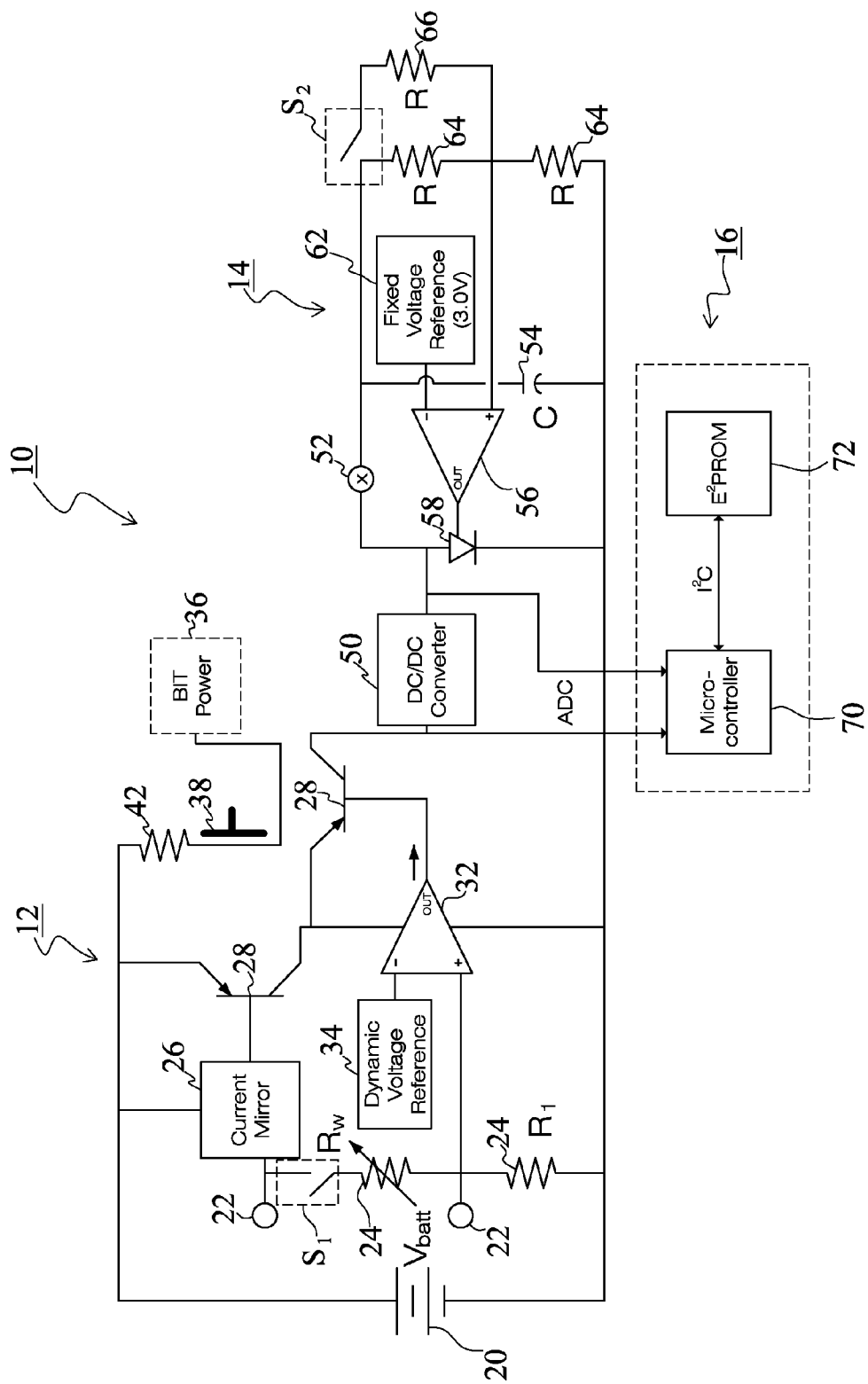
FIG. 1 is a circuit diagram illustrating the preferred conductivity sensor of the present invention.

The preferred embodiment of the sensor 10 is depicted in FIG. 1. The sensor has three subcircuits: a detection subcircuit 12, a firing subcircuit 14, and a controller subcircuit 16. As described more fully hereinafter, the detection subcircuit 12 detects the presence of saline between two associated electrodes. When salinity of a predetermined amount is detected, the firing subcircuit 14 fires the load. The controller subcircuit 16 functions to keep a record of all test conditions.

Detection subcircuit 12 is described next. It includes a battery 20 that is interconnected to a pair of electrodes 22. Battery 20 is sufficient to power the entire circuit 10. Electrodes 22 are further interconnected by a pair of resistors 24, which together form a bridge. One of the resistors is preferably a variable resistor. A switch $S_1$ can be used to selectively couple the electrodes 22 in a testing mode. One of the electrodes 22 is connected to a current mirror 26 as well as a pair of PNP transistors 28. Each of these transistors 28 includes a base, an emitter and a collector in a manner known in the art. The remaining electrode 22 is connected to the positive terminal of a comparator 32. The negative terminal of comparator 32 is connected to a dynamic voltage reference 34. The reference voltage can vary depending upon the voltage generated by battery 20. The output of the comparator 32 is connected to the firing subcircuit 14. Detector subcircuit 12 further includes a testing power source 36, a test switch 38 and a resistor 42. All of these latter components are employed in testing the sensing circuit 10 in a manner described in greater detail hereinafter.

A DC/DC converter 50 connects the detection and firing subcircuits (12 and 14). As is known, this converter 50 functions as a voltage amplifier between the two subcircuits (12 and 14). The firing subcircuit includes a load 52 for activating a release mechanism upon the presence of a pre-determined voltage. The load can be, for example, the resistive bridgewire of an electro explosive device, such as the bridgewire described in the Endres and Miller references. Load 52 is further interconnected to a capacitor 54 that is designed to fire load 52 following the discharge of the capacitor 54. Firing subcircuit 14 further includes a comparator 56, the output of which is connected to a rectifier 58. The negative terminal of the comparator 56 is connected to a fixed reference voltage 62 and the positive terminal of the comparator is connected to two resistors 64 that form a bridge. A switch $S_2$ is included for selectively placing an additional resistor 66 in parallel with the resistor bridge.

The circuit of the present invention additionally includes a controller subcircuit 16. This subcircuit 16 includes both a microcontroller 70 and an EPROM 72. This subcircuit keeps historical records regarding both the firing and detection subcircuits (12 and 14) for subsequent retrieval and analysis.

The circuit of FIG. 1 operates in the following manner. In the illustrative use of the apparatus in a canopy release mechanism, the specified all fire condition is water having a conductivity of 10,000 micromhos or greater, i.e. seawater. Prior to electrodes 22 being exposed to such water, and with test switch $S_1$ opened, there is no output signal at the output of comparator 32. As a result, the PNP transistors 28 are closed and no signal is received by the firing subcircuit 14. This results in an open circuit in the path that includes the capacitor 54, the rectifier 58 and the load 52. In this open circuit configuration, there is likewise no current flow path directly between electrodes 22 nor through battery 20.

When electrodes 22 are exposed to water of sufficient conductivity, current flows from the battery 20 through the water and between electrodes 22. As a result, an output signal is created at the output of comparator 32. This, in turn, results in an output at the emitter of the final PNP transistor 28, whereby current is supplied to the firing subcircuit 14. Provided that switch $S_2$ is opened, voltage provided to the positive terminal of comparator 56 will be greater than the fixed reference voltage 62, such that there is an output from comparator 56. This output permits current flow through rectifier 58, which, in turn, charges capacitor 54. Once capacitor 54 is fully charged, current flows to load 52 so as to fire the electro explosive device.

The test mode of the present invention will be described next. A user can initiate the test mode by depressing the test switch 38. This has the effect of closing switches $S_1$ and $S_2$. Closing switch $S_1$ bridges the two electrodes 22 so that current flows from battery 20 in the absence of salt water. Again, as noted above, this results in an output from comparator 32 and from PNP transistor 28 to provide voltage to firing subcircuit 14. However, because switch $S_2$ is also closed during the testing mode the voltage supplied to positive terminal of comparator 56 does not increase pass the fixed reference voltage 62. This is a result of the decreased resistance from bringing the additional resistor 66 in parallel. As a result, there is no output from comparator 56 and rectifier 58 prevents the flow of current to capacitor 54. Capacitor is, therefore, not charged and load 52 is not fired. However, during this testing mode, a signal is provided to the controller subcircuit 16 to otherwise verify the integrity of circuit 10. Historical data regarding circuit testing can be stored in EPROM 72.

Figure 2:
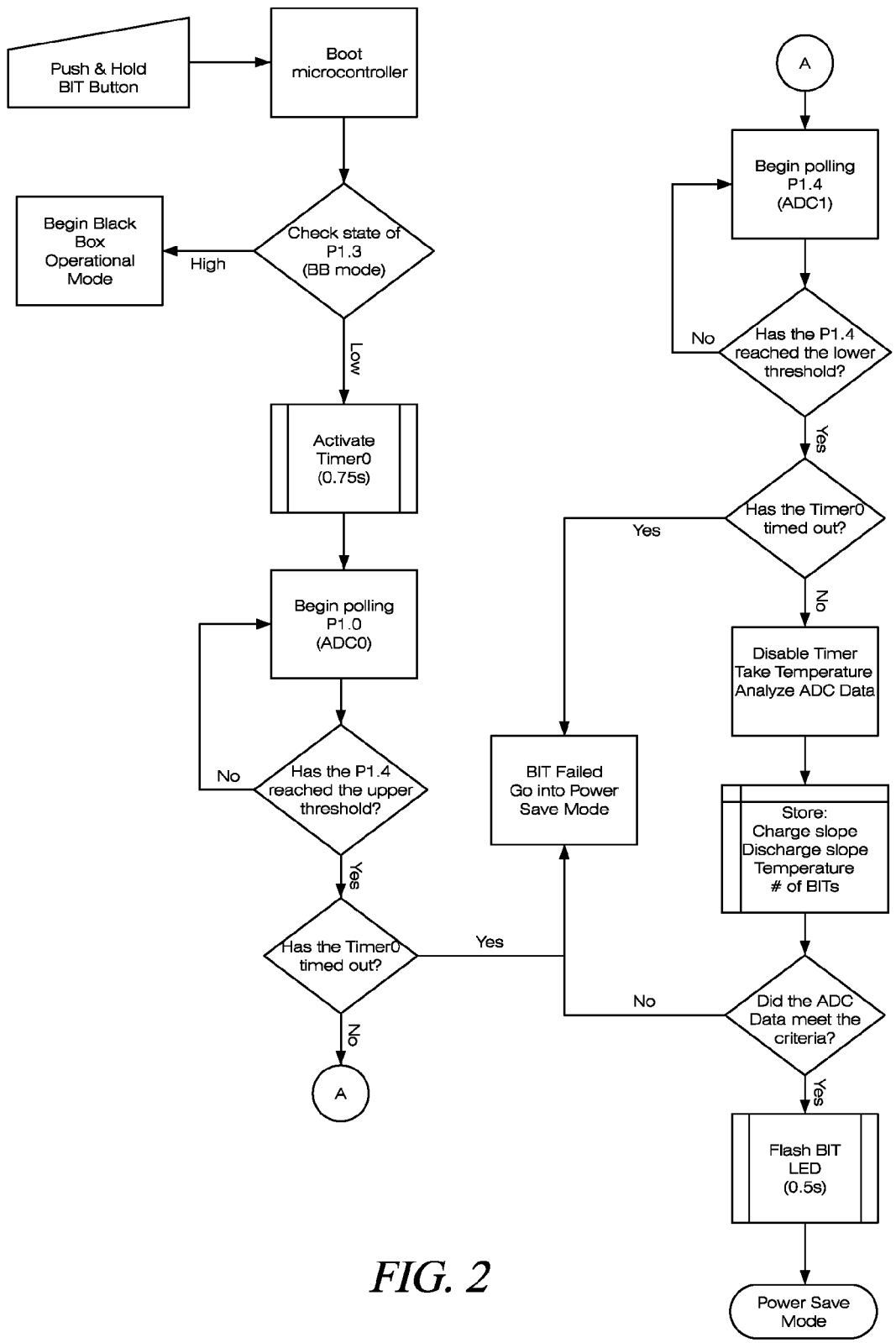
FIG. 2 is a flow chart illustrating the steps associated with the preferred method of the present invention.

The software implementation of the circuit of the present invention is depicted by way of the flowchart of FIG. 2. This flowchart illustrates how microcontroller initiates a timed sequence during which the aforementioned testing mode is carried out. The chart illustrates a data gathering step, whereby data relating to the charge and discharge slopes of capacitor 54 are stored. Historical data regarding testing is also gathered during this step.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A sensor (10) for use in conjunction with a canopy release mechanism, the sensor (10) having firing and testing modes and comprising:

a detection sub-circuit (12) including a battery (20) and first and second electrodes (22), the detection sub-circuit (12) further including a first switch (S1) having a closed position completing a circuit between the first and second electrodes (22) and an opened position with no circuit being completed between the first and second electrodes (22);

a firing sub-circuit (14) connected to the detection sub-circuit (12), the firing sub-circuit (14) including a comparator (56) having positive and negative terminals and a comparator output, a capacitor (54) and a load (52) interconnected to the comparator output, a fixed reference voltage (62) connected to the negative terminal, a second switch (S2) interconnected to the positive terminal, and two resistors, the second switch (S2) having a closed position wherein the two resistors are placed in parallel whereby the fixed reference voltage (62) is not exceeded and there is no output from comparator (56), the second switch (S2) further including an opened position wherein current flow at the comparator output is permitted;

a test switch (38) and an associated test power source (36), closure of the test switch (38) effecting closure of the first and second switches (S1 and S2);

a controller sub-circuit (16) connected to the detection sub-circuit (12) and including a microcontroller (70) and an EPROM (72), the controller sub-circuit (16) functioning to record data regarding the firing mode;

whereby the firing mode is achieved when the test switch (38) is opened and sea water is present to complete a circuit between the first and second electrodes (22), the completed circuit delivering current to the firing subcircuit (14), the opening of second switch (S2), permitting current flow at the comparator output to charge capacitor (54) and fire load (52); and whereby the testing mode is achieved when the test switch (38) is closed to complete a circuit between the first and second electrodes (22), the complete circuit delivering current to the firing sub-circuit (14), the closing of second switch (S2) preventing current flow at the comparator output, whereby capacitor (54) is not charged and load (52) is not fired, current being supplied to the controller sub-circuit (16) during the testing mode.

2. A sensor (10) comprising:

a detection sub-circuit (12) including first and second electrodes (22), the detection sub-circuit (12) further including a first switch (S1) having a closed position completing a circuit between the first and second electrodes (22) and an opened position with no circuit being completed between the first and second electrodes (22);

a firing sub-circuit (14) connected to the detection sub-circuit (12), the firing sub-circuit (14) including a comparator (56) having a comparator output, a load (52) interconnected to the comparator output, a second switch (S2) connected to the comparator (56), wherein the comparator (56) includes first and second inputs in addition to an output, and wherein a fixed reference voltage (62) is connected to the first input and the second switch (S2) is connected to the second input, the firing sub-circuit (14) further comprising two resistors wherein closing the second switch (S2) places the two resistors in parallel whereby the fixed reference voltage (62) is not exceeded, there is no output from comparator (56), and the load (52) cannot be fired.

3. The sensor as described in claim 2 further comprising a test switch (38) for selectively opening or closing the first and second switches (S1 and S2).

4. the sensor (10) as described in claim 3 wherein the sensor (10) includes a firing mode that is achieved when the test switch (38) opened and sea water is present to complete a circuit between the first and second electrodes (22), the completed circuit delivering current to the firing sub-circuit (14), the opening of second switch (S2) permitting current flow at the comparator output to fire load (52).

5. The sensor (10) as described in claim 4 wherein the sensor (10) also includes a testing mode that is achieved when the test switch (38) is closed to complete a circuit between the first and second electrodes (22), the complete circuit delivering current to the firing sub-circuit (14), the closing of second switch (S2) preventing current flow at the comparator output, whereby load (52) is not fired.

6. The sensor (10) as described in claim 5 further comprising a controller sub-circuit (16) for recording data regarding the firing mode.

7. The sensor (10) as described in claim 6 wherein a normal condition is recorded when sensor (10) is in the testing mode and current is recorded by controller sub-circuit (16).

8. The sensor (10) as described in claim 6 wherein a failure to condition is recorded when the sensor (10) is in the testing mode but no current is recorded by controller sub-circuit (16).

9. The sensor (10) as described in claim 2 further comprising a capacitor (54) and the load (52) that are connected to the output of comparator (56) whereby when there is current at the output of comparator (56) the capacitor (54) triggers the load (52).

10. The sensor (10) as described in claim 9 further comprising a canopy release mechanism that is triggered by the load (52).

11. A sensor (10) comprising:

a detection sub-circuit (12) including first and second electrodes (22), the detection sub-circuit (12) further including a first switch (S1) having a closed position completing a circuit between the first and second electrodes (22) and an opened position with no circuit being completed between the first and second electrodes (22);

a firing sub-circuit (14) connected to the detection sub-circuit (12), the firing sub-circuit (14) including a load (52), a comparator (56) having a comparator output, wherein the comparator (56) includes first and second inputs in addition to an output, and wherein a fixed reference voltage (62) is connected to the first input and a second switch (S2) is coupled to the second input, the firing sub-circuit (14) further comprising two resistors wherein closing the second switch (S2) places the two resistors in parallel whereby the fixed reference voltage (62) is not exceeded, there is no output from comparator (56), and load (52) cannot be fired;

whereby the circuit (10) has a firing mode wherein both the first and second switches (S1-S2) are opened and a testing mode wherein both the first and second switches (S1-S2) are closed;

a controller sub-circuit (16) connected to the detection sub-circuit (12) and firing sub-circuit (14) and including a microcontroller (70) and an EPROM (72), the controller sub-circuit (16) functioning to record data regarding the firing mode.

12. The sensor as described in claim 11 wherein the microcontroller (70) initiates the testing mode in a timed sequence.

13. The sensor as described in claim 11 wherein a capacitor (54) is used to fire load (52).

14. The sensor as described in claim 13 wherein the controller sub-circuit (16) records the charge and discharge slopes of the capacitor (52).

* * * * *

UNITED STATES PATENT AND TRADEMARK OFFICE
CERTIFICATE OF CORRECTION

PATENT NO. : 8,324,903 B2
APPLICATION NO. : 12/646137
DATED : December 4, 2012
INVENTOR(S) : Andre Cournand It is certified that error appears in the above-identified patent and that said Letters Patent is hereby corrected as shown below:

In the Specifications:

Col. 4, line 16, "microcontroller initiates" should be "microcontroller 70 initiates".

Signed and Sealed this
Twentieth Day of August, 2013

Teresa Stanek Rea
*Acting Director of the United States Patent and Trademark Office*